(12) United States Patent
Soller

(10) Patent No.: US 6,482,365 B1
(45) Date of Patent: Nov. 19, 2002

(54) VOLATILE DISPENSER LAMP

(75) Inventor: Douglas A. Soller, Mt. Pleasant, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/952,331

(22) Filed: Sep. 14, 2001

(51) Int. Cl.⁷ .................................................. A01L 9/00
(52) U.S. Cl. ........................ 422/126; 422/125; 43/125; 43/127
(58) Field of Search ................................ 422/125, 126; 43/124–129

(56) References Cited

U.S. PATENT DOCUMENTS

| 692,075 A | 1/1902 | Searle |
| 2,742,342 A | 4/1956 | Dew et al. |
| 3,279,118 A | 10/1966 | Allen |
| 4,781,895 A | * 11/1988 | Spector ........................ 422/125 |
| 5,657,574 A | * 8/1997 | Kandathil et al. ............. 43/125 |
| 6,033,212 A | 3/2000 | Bonnema et al. |
| 6,061,950 A | * 5/2000 | Carey et al. ................... 43/125 |

FOREIGN PATENT DOCUMENTS

| WO | WO 00/78135 | 12/2000 |
| ZA | 9405537 | 10/1996 |

* cited by examiner

Primary Examiner—Robert J. Warden, Sr.
Assistant Examiner—Sean E. Conley

(57) ABSTRACT

A lamp dispenses a volatile material, such as an insecticide, from a burnable coil. There is a flame source mounted on a base, a chimney, a coil support, and a burnable coil supported on the coil support above the flame. The flame provides light, heats the coil to some extent, and provides convection for dispersal of the volatile. A kit for replacing the candle and coil consumed during use is also disclosed, as are methods of use of such lamps.

14 Claims, 5 Drawing Sheets

VOLATILE DISPENSER LAMP

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

This invention relates to dispensers for volatile materials such as insect control agents, scents and the like. In particular, the invention relates to dispensers that simultaneously dispense a volatile from a burnable coil and provide illumination.

There are a number of known dispensers for volatile ingredients that provide the additional feature of lighting the surrounding area. For example, U.S. Pat. No. 6,033,212 discloses a lantern that burns fuel for light. The flame is contained in a glass, transparent globe that is covered at its top. The cover has a slot that receives a pad impregnated with a volatile material having an insect control agent. The waste heat from the burning fuel exits the globe through the slot, which heats the pad and releases the volatile.

WO 00/78135 is another approach for mounting an insect repellent impregnated pad adjacent a flame. However, the types of pads used with these designs can be somewhat costly to produce, and in some cases place constraints on the type of active that can be used.

Citronella candles also provide both light and an insect repellent, and do so relatively inexpensively. However, exposed candle flames can be snuffed by the wind, and not all actives can survive being directly exposed to the candle flame when the candle wax is burnt.

Insect (e.g. mosquito) coils are also well known. They are typically a spiral coil of compressed, largely pulp material which has been impregnated with an insect control active. The coils can alternatively (or in addition) contain other active ingredients having different characteristics, such as aromatics or disinfectants. These coils are extremely inexpensive, and due to their slow burn rate provide overnight protection. They are particularly desirable because of their ability to disperse a variety of very effective insecticidal actives, at low cost.

However, these coils can be snuffed out if they are exposed to too much wind. Thus, it has been proposed to house them in apertured pots that can prevent outside gusts from directly reaching the coil. See e.g. U.S. Pat. No. 6,061,950. These pots also have the benefit of inhibiting persons from accidently bumping into these coils while they are burning. However, these pots dispense active at a slower rate than a coil that is directly open to the air, thus requiring them to be started somewhat earlier before using an area that might be insect infested.

Some other structures have been proposed to dispense insecticidal control agents by mounting materials containing them adjacent a heat source. See e.g. U.S. Pat. Nos. 692,075, 2,742,342 and 3,279,118. However, to date the art has not proposed a way to mount a mosquito coil in a lamp in a way in which the lamp flame assists in the dispersion of the vapors from the coil, without causing the entire coil to start burning out of sequence. Thus, there is still a need for an improved combined lamp and volatile dispensing device.

SUMMARY OF THE INVENTION

In one aspect the invention provides a lamp for dispensing a volatile material. There is a flame source, a chimney mounted around the flame source, a support mounted to the chimney above the flame source, and a burnable coil having a volatile material. The coil is positioned above the flame source so as to be exposed to heat therefrom.

In preferred forms the support is a plate having an opening (preferably a plurality of openings) there through. The support may also have a raised element (a spade) for supporting the coil, with the coil being mounted adjacent an upper opening of the chimney, vertically above the flame source. The chimney can have a radially inwardly extending ledge on which the support rests.

There is also preferably a skirt-like base upon which the flame source and chimney are mounted, an upper surface of the base having a recess for receiving a lower edge of the chimney. The base includes a plurality of openings positioned radially outside of the recess and a plurality of openings positioned radially inward of a radially outer edge of the recess. Air may pass inward through the radially outside openings, and then up through the chimney via the radially inward openings.

In other preferred forms, the recess includes a central depression for receiving the flame source, the flame source is a cup containing a candle, and the cup has a bottom with a recess sized to receive an upwardly extending mounting post of the cover. The support can optionally have a collector tray suspended below a top wall opening of the support so as to collect ashes, and/or the support top wall can include a recessed central section having no vertical openings there through, and a radially outward section having an opening there through.

The additional heat which builds up due to air flow through outer peripheral openings can be taken advantage of. There can be a faster release of active near the outside of the coil (as that portion is exposed to more heat). This enables an area to be adequately treated very soon after the device is lit. If desired, this effect can be enhanced by providing a higher concentration of active (per unit mass) near the outer periphery, and/or two different types of active (the more potent being on the outer periphery).

In another aspect, the invention provides a kit providing a replacement coil and candle for lamps of the above kind. A cup for housing the candle (e.g. one which interfits with the base) may also be supplied with the kit.

Still another aspect of the invention provides a method for controlling flying insects. One provides a lamp of the above kind, lights the coil and the flame source, and permits volatizable material to pass from the coil and out the chimney so as to expose an area to the volatizable material. The volatizable material is an insect control agent.

Preferred insect control agents are insecticides, repellents, and insect growth regulators. A wide variety of insect control agents of this type are known. The preferred ones are those which have previously been incorporated into mosquito coils, such as d-cis/trans allethrin.

Because the lamp provides both light and insect control, and does so even in windy environments, it is particularly suitable for use during a backyard barbecue, around sunset. The device is designed to utilize extremely inexpensive consumables (e.g. standard conventional burnable coils; standard wax candles).

The flame source serves multiple purposes. It provides light, while also creating convection to draw outside air past the burning coil. The air/volatile mix is then propelled out the top of the chimney to widely and quickly disperse the active.

The foregoing and other advantages of the present invention will appear from the following description. In that description, reference is made to the accompanying drawings which form a part hereof and in which there is shown by way of illustration preferred embodiments of the invention. These embodiments do not represent the full scope of the invention. Rather, reference should be made to the claims for interpreting the full scope of the invention.

DETAILED DESCRIPTION OF THE PREFERRED EMBODIMENTS

Figure 1:
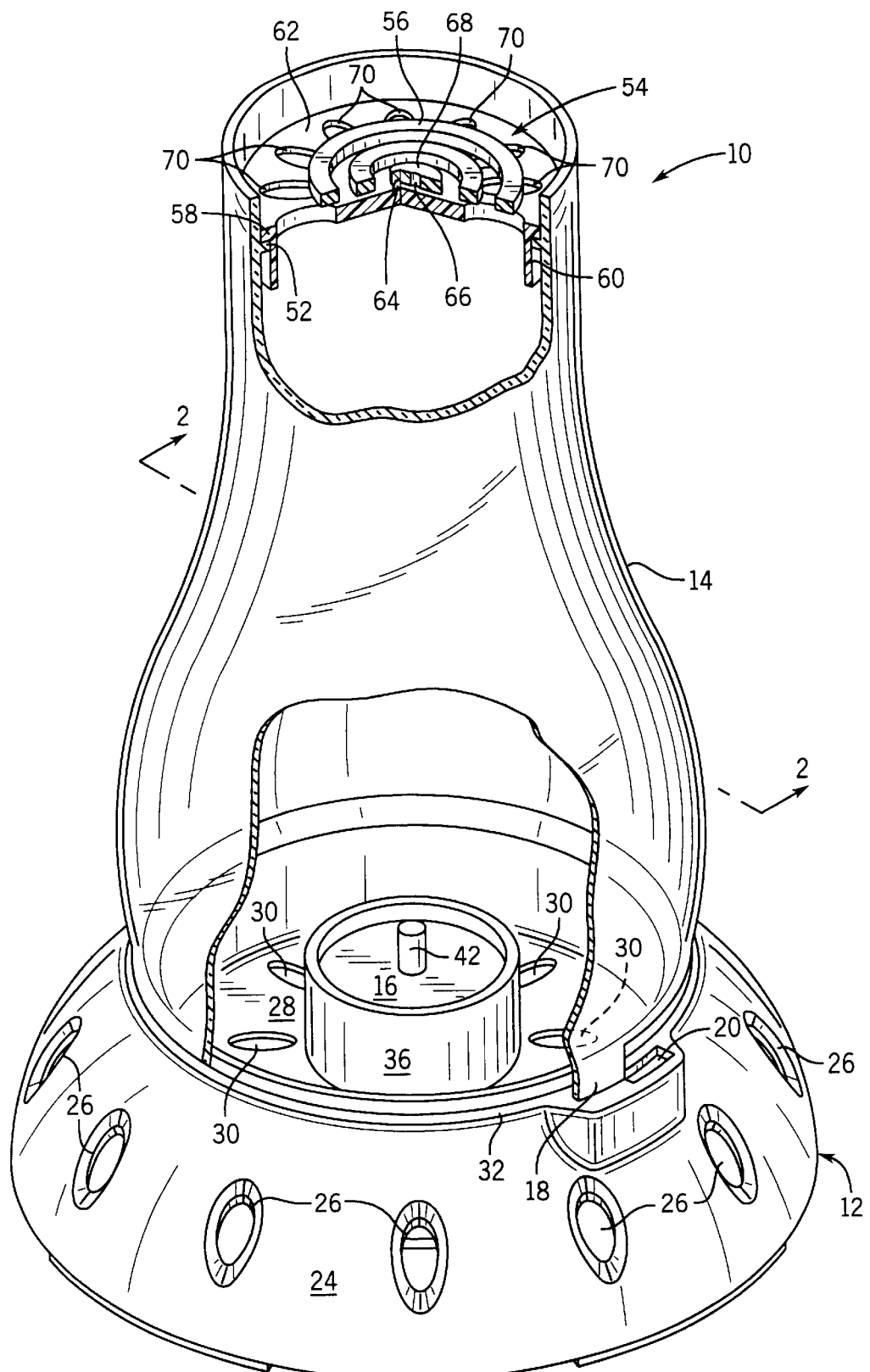
FIG. 1 is a cut-away perspective view of a lamp of the present invention.
Figure 2:
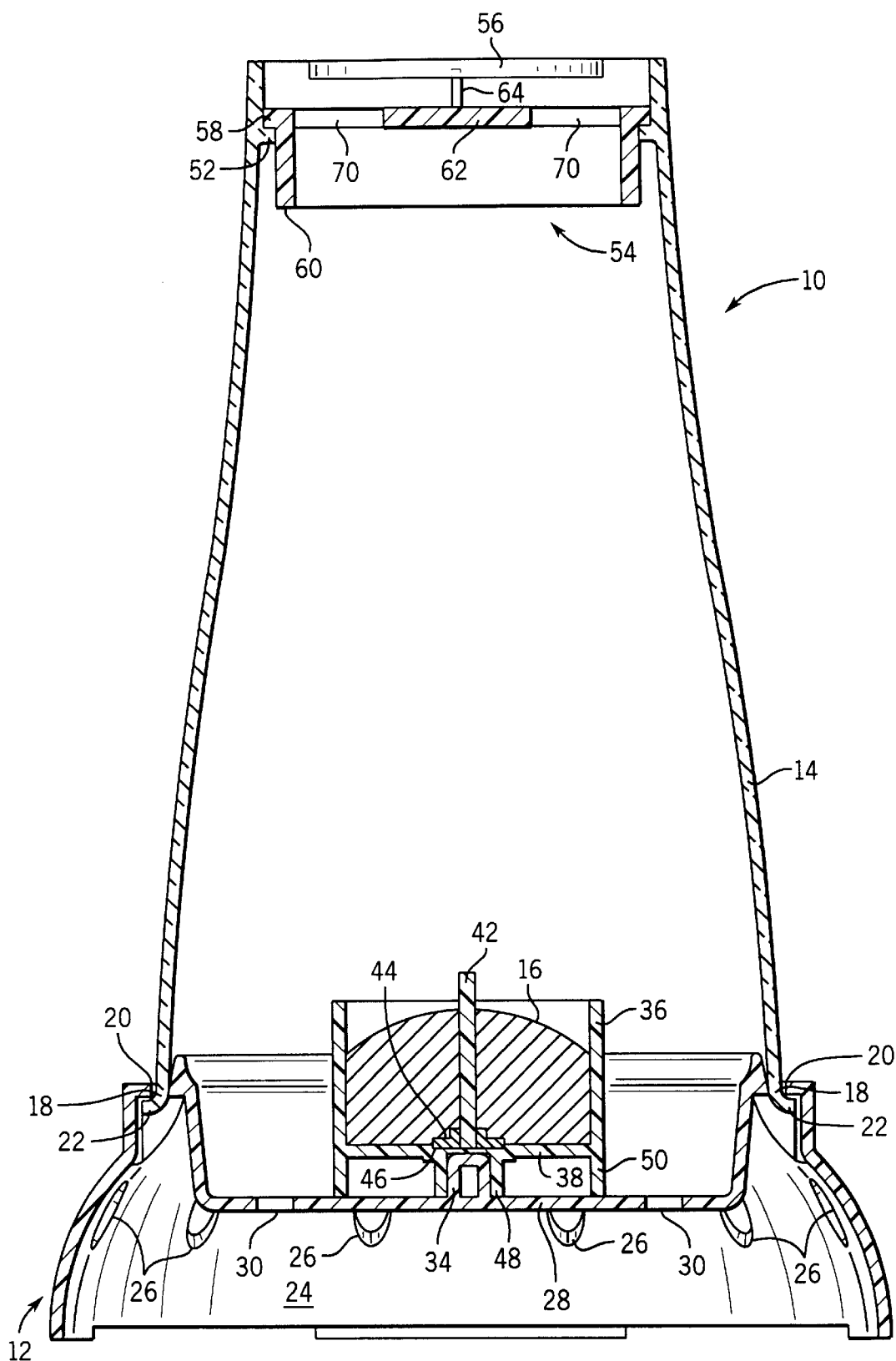
FIG. 2 is a cross sectional view thereof, taken along line 2—2 of FIG. 1.
Figure 3:
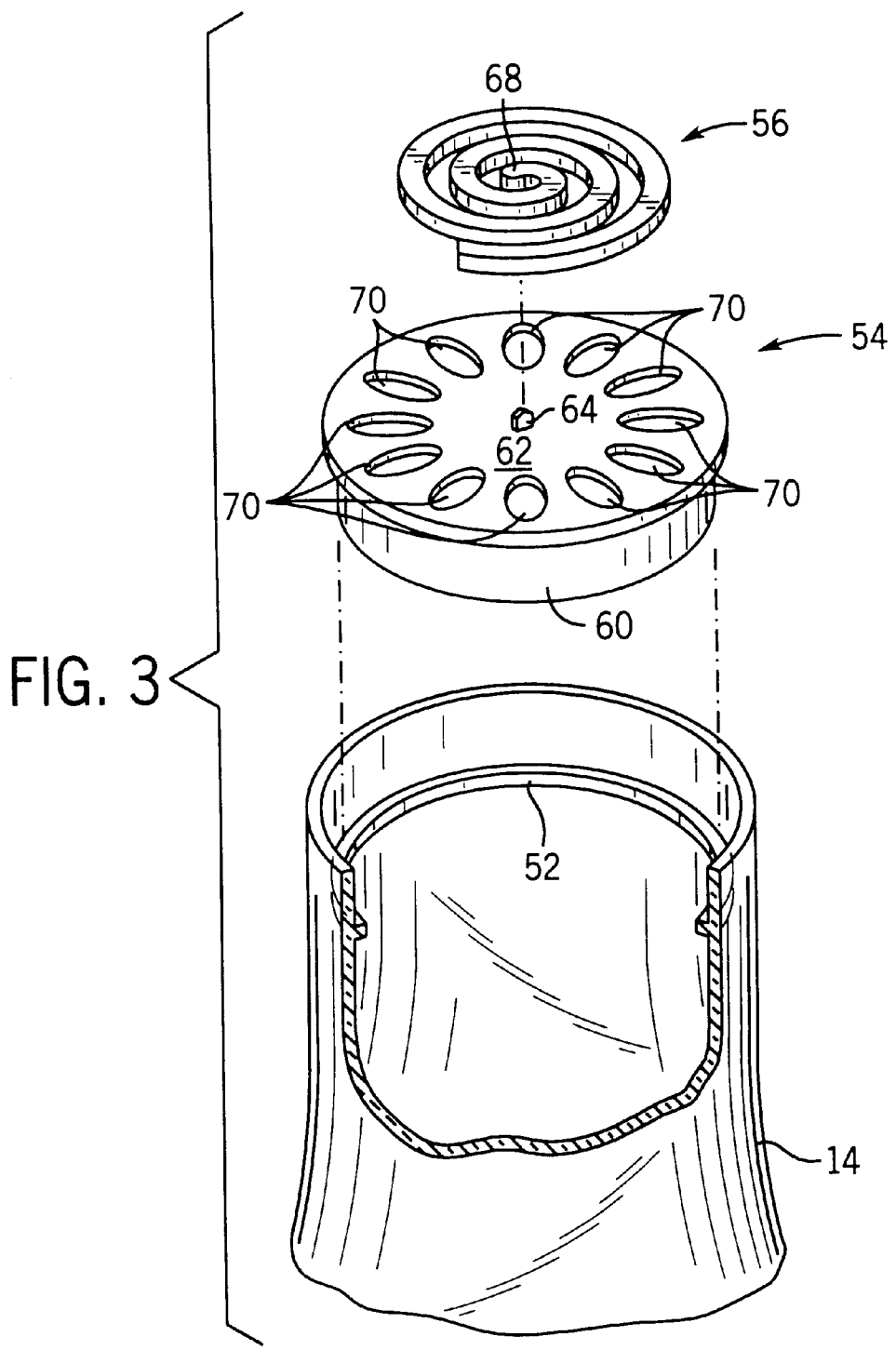
FIG. 3 is a partial exploded perspective view thereof, with a portion of the chimney cut away.

Referring now to FIGS. 1–3 of the present application, a lamp 10 includes a base 12 supporting a removable, open-ended chimney 14 and a removable candle 16. The chimney 14 can be made of glass or, preferably, a heat-resistive plastic, such as a V-O flame rated polycarbonate, commercially available under the name "Makrolon® 6455" from Bayer Corporation. The chimney 14 can be translucent to allow light to pass there through while obscuring the inside of the chimney, or alternatively could be transparent.

The chimney 14 attaches to the base 12 with bayonet style locking tabs/legs 18 formed on the lower edge of the chimney 14 that mate with locking slots 20 formed in the top of the base 12. The legs 18 have bent feet 22 (see FIG. 2) that pass through an enlarged area of each slot 20, but cannot pass through a narrow area of each slot 20. Thus, the chimney 14 is locked to the base 12 when the legs 18 are rotated into the narrow area of the slots 20.

The base 12 has a skirt 24 extending around its periphery and having a plurality of outer ventilation openings 26 spaced apart around the wall 24. The base 12 also has a recessed top wall 28 with a plurality of spaced inner openings 30. Thus, the outer openings 26 are open to the outside air and the inner openings 30 are at the interior of the chimney 14 so that air can pass into the base 12 and up into the chimney 14. The top wall 28 is formed with a circular shelf 32 against which rests the bottom of the chimney 14. At the center of the top wall 28, and thus the base 12, is an upwardly extending mounting post 34 for mounting the candle 16.

The candle 16 is contained in a candle cup 36 having a floor 38 and a cylindrical wall 40 defining an open top. The candle cup 36 is preferably made of a V-O flame rated polycarbonate material. The candle 16 is preferably a conventional cylindrical paraffin wax candle having a wick 42 held at the bottom by a wick clip 44 disposed in a depression 46 in the cup floor 38 to restrict movement of the candle 16. A downwardly opening cylindrical socket 48 extends from the center of the cup floor 38 as does a cylindrical cup support member 50 at the periphery of the cup floor 38. The support member 50 is at least as tall as the socket 48 to allow the candle cup 36 to sit upright on top of the base 12. The cup socket 48 engages the mounting post 34 to grip the candle cup 36 to the base 12 so that the candle 16 does not tip over or move with respect to base 12. The lower half of lamp 10 is preferably identical to the FIGS. 16–20 embodiment of WO 00/78135. Thus, further details regarding its preferred construction can be obtained by reading that publication.

In accordance with the present invention, the chimney 14 preferably includes a circular ledge 52 extending radially inwardly into its interior on which rests a coil support 54 supporting a burnable coil 56. The burnable coil 56 is impregnated with (e.g. the material is mixed with, coated with or otherwise carries) a volatile material. Our preferred insect control active is d-cis/trans allethrin. The coil 56 is conventional (e.g. has a spiral configuration and is otherwise of the type disclosed in U.S. Pat. No. 6,066,950, e.g. see U.S. Pat. No. 5,657,574), the disclosures of which are incorporated by reference herein.

The coil support 54 that is shown is a disk-shaped body having a circumferential lip 58 extending radially outward beyond an annular skirt 60. The lip 58 rests on the chimney ledge 52 to mount the coil support 54 near the top opening of the chimney 14. The coil support 54 has a top wall 62 with a spade 64 extending up from its center. The spade 64 is sized to fit in a recess 66 in a mounting end 68 of the coil 56. The spade 64 thus can support the coil 54 spaced off the top wall 62 to reduce the occurrence of a burning coil 54 being inadvertently snuffed out during use due to losing heat to the support.

The wall 62 also has a plurality of ventilation openings 70 there through allowing air to pass through the coil 56 and exit the chimney 14. The coil support 54 is preferably made of metal.

The lamp 10 is used by removing the chimney 14 temporarily to light the candle 16. The chimney 14 then re-attached to the base and the coil 56 is placed onto the spade 64 and its free end is lit. A convective air flow is generated by the heat from the candle 16, which pulls outside air into the base 12 through the openings 26 and up through openings 30 into the chimney 14, past the candle 16. The air stream is then drawn up through the chimney 14 and through the openings 70 in the coil support 54 past the burning coil 56, where the air stream mixes with the volatile material released from the burning coil 56. The volatile laden air then passes out through the top of the chimney 14 to the surrounding outside air.

The openings 26 and 30 in the base 12 increase air flow through the chimney 14 to provide the proper ventilation to the candle 16 and the coil 18. The chimney draft does not extinguish the coil 18, in part due to the heat from the candle vapors transferred to the coil through the coil support 54.

The outside air pulled through the base 12 is cool relative to the air surrounding the open flame of the candle 16. Thus, the surrounding lower wall of the chimney 14 is cooled by the air flow from below.

Figure 4:
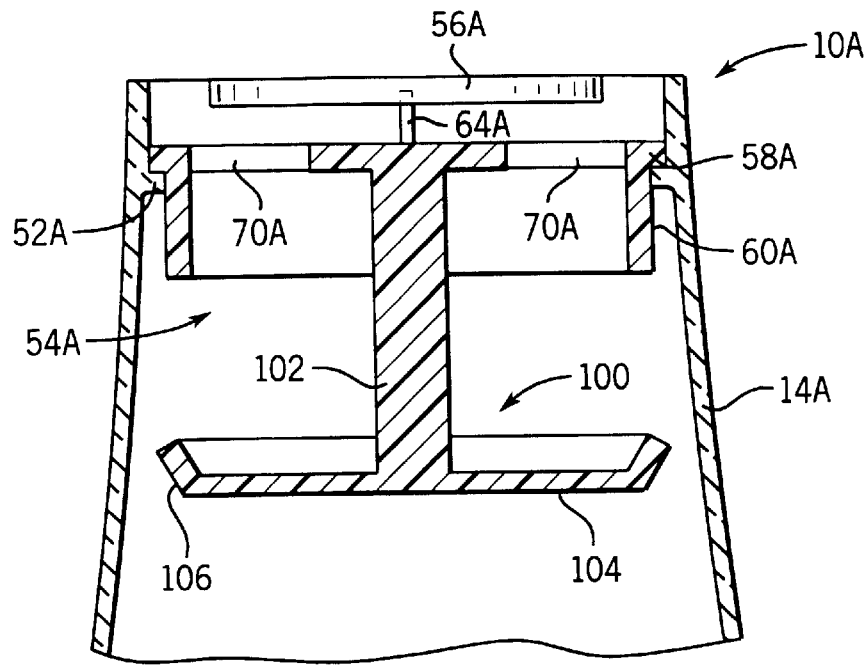
FIG. 4 is a partial cross sectional view, similar to FIG. 2, albeit of an alternative embodiment.

FIG. 4 shows a partial cross-sectional view of an alternate embodiment of the dispenser lamp. Elements of this embodiment similar to those described above are referred to herein with similar reference numerals, albeit with the suffix "A". The elements of this embodiment are identical to the embodiment described above, except for an ash catcher tray 100. Specifically, the dispenser lamp 10A includes a base (not shown) mounting a candle (not shown) and a translucent chimney 14A. The chimney 14A has an inner ledge 52A extending into its interior on which rests the coil support 54A supporting a burnable coil 56A of the type described above.

The disk-shaped coil support 54A has a circumferential lip 58A extending radially outward beyond an annular skirt 60A. The lip 58A rests on the chimney ledge 52A to mount the coil support 54A near the top opening of the chimney 14A. The coil support 54A has a top wall 62A with a spade 64A extending up from its center supporting the coil 54A off the top wall 62A. The top wall 62A has a plurality of ventilation openings 70A there through allowing air to exit the chimney 14A and pass through the coil 56A.

The catcher tray 100 is suspended beneath the openings 70A in the top wall 62A by a hanger member 102.

The tray 100 has a circular bottom 104 and an upwardly extending peripheral wall 106. The tray 100 can catch and contain partially burnt segments of the coil 56A that may fall through the openings 70A in the top wall 62A.

The tray 100 reduces mess and more importantly prevents coil cinders from falling onto the candle. The tray 100 can be molded integrally with the hanger member 102 and top wall 62A (as shown), or these elements can be separately formed and then connected in any suitable manner, such as a snap fit or threaded fastener. If separately formed, the hanger and/or the tray could be made of metal. In any event, the tray 100 will also serve to disrupt the flow path of the air stream though the chimney 14A. In particular, it will force the air column in the center of the chimney 14A to flow outwardly to pass around its periphery. The air will then flow back toward the center of the chimney 14A, up through the openings 70A in the coil support 54A and out of the chimney 14A. This mixes the heat effect across the radius of the chimney opening, thereby providing for more uniform heating.

Figure 6:
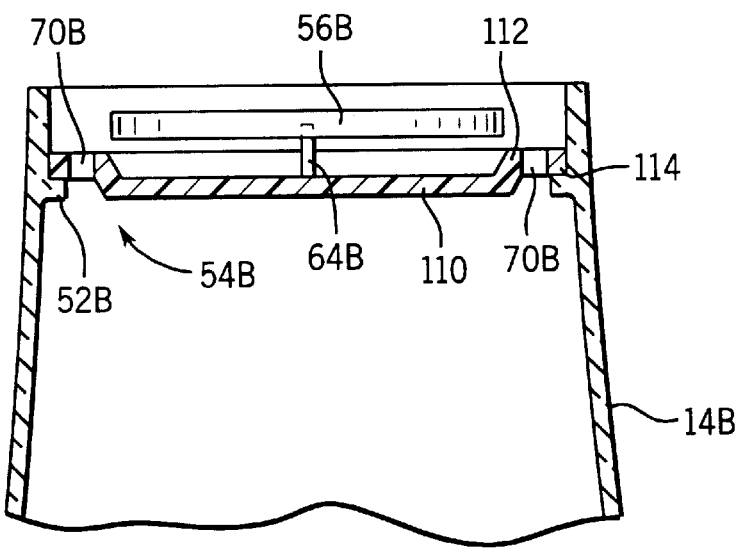
FIG. 6 is a cross sectional view thereof taken along line 6—6 of FIG. 5.
Figure 5:
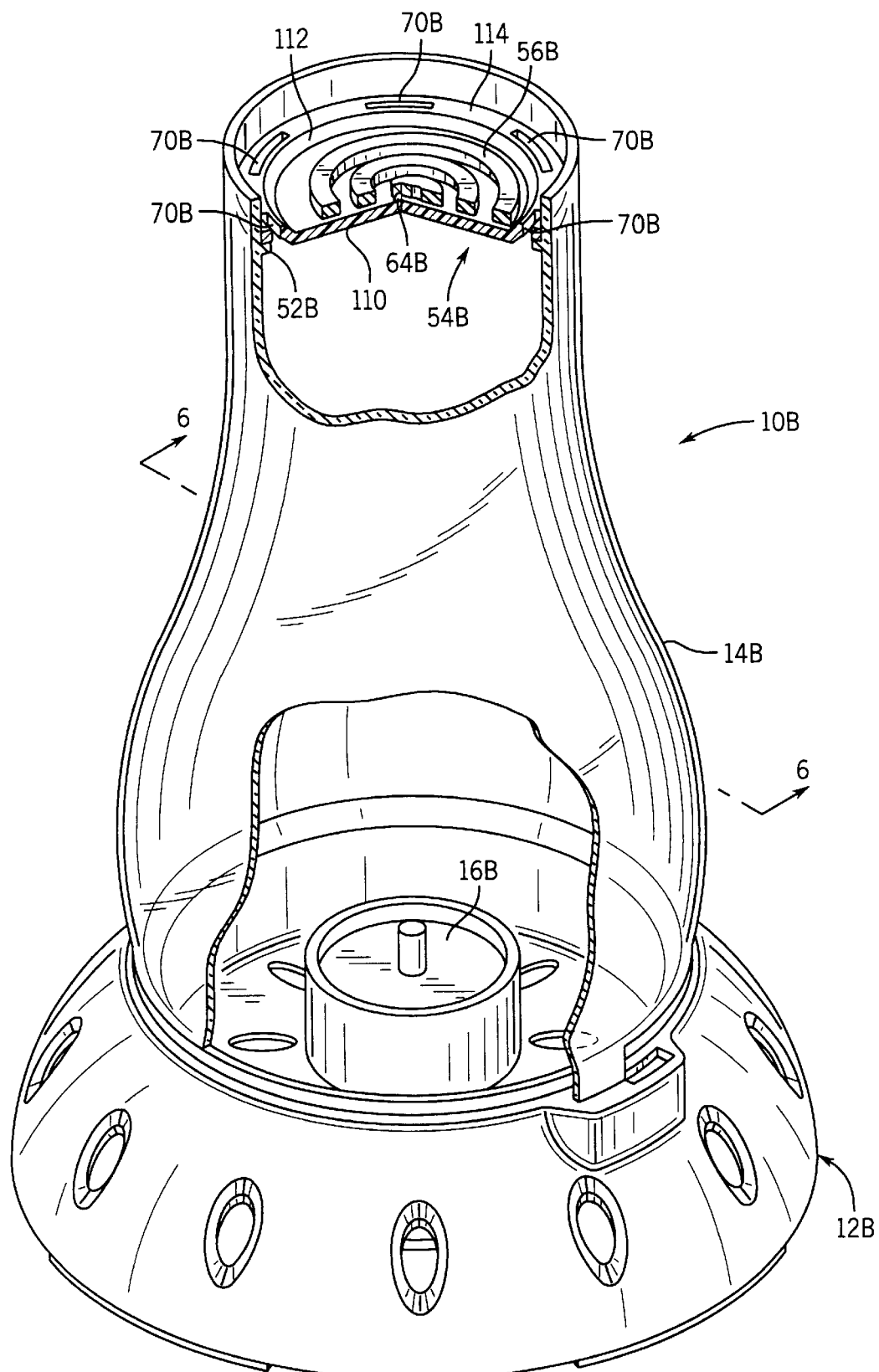
FIG. 5 is a cut-away perspective view of another alternative embodiment.

FIGS. 5 and 6 illustrate another alternate embodiment of the dispenser lamp. Elements of this embodiment similar to those described above are referred to herein with similar reference numerals, albeit with the suffix "B". The elements of this embodiment are identical to the embodiment described above, expect for the coil support. Specifically, the dispenser lamp 10B includes a base 12B mounting a candle 16B and a translucent chimney 14B identical to that of the first described embodiment. The chimney 14B has an inner ledge 52B extending into its interior on which rests the coil support 54B supporting a burnable coil 56B of the type described above.

The support 54B forms a shallow tray having a bottom 110 and an upwardly extending annular wall 112 from which extends radially outward an annular flange 114 that rests on the chimney ledge 52B to mount the coil support 54B near the top opening of the chimney 14B. The bottom 110 has a spade 64B extending up from its center supporting the coil 54B in the air. The tray can catch and contain burnt segments of the coil 56B that fall to reduce mess and prevents embers from falling onto the candle. The flange 114 has a plurality of ventilation slots 70B there through allowing air to exit the chimney 14B and pass around the periphery of the coil 56B. The tray will force the air column in the center of the chimney 14B to flow outwardly to the slots 70B past the periphery of the coil 56B and out of the chimney 14B.

The invention thus provides a device particularly suitable for use as a combined outdoor lantern and insect control device. The lantern utilizes conventional burnable coils, and in a preferred form inexpensive candles. Given the exposure of the coil to the flame heat, coil burning is somewhat more rapid than is conventional for coils. Thus, this device provides quicker coverage, but may be more suitable for use at a four hour cookout rather than as an overnight camping light.

The candle is preferably made of paraffin wax by a process of bonding small wax granules in a compression mold. This technique is well known for producing candles with consistent dimensions and densities. The preferred candle weighs from 15 to 20 grams with a diameter of about 37 mm and has an overall height of about 20 mm at its center. A candle of this size will burn for about 4 hours.

Exhausted coils are replaced by removing any remaining non-burnt section of the coil, emptying the ash and attaching the mounting end of the replacement coil from the kit to the spade of the coil support. Exhausted candles are replaced by removing the chimney from the base, removing the old candle cup and attaching the replacement candle from the kit to the base by pressing the socket onto the mounting post. In a preferred form of the kit, the candle will also have a candle cup which houses it.

Preferred embodiments of the invention have been described above. However, these embodiments are intended to be illustrative, and not exhaustive. For example, while the dispenser is shown and described for use with an insect control active, it could instead be used to dispense aromatics, disinfectants or other volatiles. Thus, the claims should be looked to in order to assess the full scope of the invention.

INDUSTRIAL APPLICABILITY

The present invention provides an apparatus providing illumination and dispensing volatiles useful, among other things, to repel insects.

I claim:

1. A lamp for dispensing a volatile material, comprising:

a flame source;

a chimney mounted around the flame source;

a support mounted to the chimney above the flame source and having an opening in communication with an interior of the chimney below the support; and a burnable coil having a volatile material, the coil being positioned above the flame source so as to be exposed to heated air when the flame source is lit so as to be ventilated by said heated air from the flame source that has passed through the support from a portion of the chimney below the support.

2. The lamp of claim 1, wherein the support has a raised spade for supporting the coil.

3. The lamp of claim 1, wherein the coil is mounted adjacent an upper opening of the chimney, in a position vertically above the flame source.

4. The lamp of claim 1, wherein the chimney has a radially inwardly extending ledge on which the support rests.

5. The lamp of claim 1, further comprising a base upon which the flame source and chimney are mounted.

6. The lamp of claim 5, wherein an upper surface of the base has a recess for receiving a lower edge of the chimney, and the base includes a plurality of openings positioned radially outside of the recess and a plurality of openings positioned radially inward of a radially outer edge of the recess, whereby air may pass inward through the radially outside openings, and then up through the chimney via the radially inward openings.

7. The lamp of claim 6, wherein the recess includes a central depression for receiving the flame source.

8. The lamp of claim 1, wherein the flame source comprises a candle and a cup for housing the candle.

9. The lamp of claim 8, wherein the cup has a bottom with a recess sized to receive an upwardly extending mounting post of a base member.

10. The lamp of claim 1, wherein the support includes a collector tray suspended below a top wall of the support having the opening.

11. The lamp of claim 1, wherein the support top wall includes a recessed central section having no openings there through, and a radially outward section having the opening.

12. The lamp of claim 1, wherein the burnable coil has a higher concentration of volatile material per mass of the coil near its outer periphery than near its inward end.

13. The lamp of claim 1, wherein the burnable coil has at least two different volatile materials dispersed non-uniformly in the coil.

14. A method for controlling flying insects, comprising:
providing a lamp of claim 1;
lighting the coil and the flame source; and
permitting volatazable material to pass from the coil out the chimney so as to expose an area to the volatizable material;
wherein the volatizable material is an insect control agent.

* * * * *